(12) United States Patent
Colman (10) Patent No.: US 9,149,623 B1
(45) Date of Patent: Oct. 6, 2015

(54) ADAPTERS

(71) Applicant: ORIDION MEDICAL 1987 LTD., Jerusalem (IL)

(72) Inventor: Joshua Lewis Colman, Jerusalem (IL)

(73) Assignee: Oridion Medical 1987 Ltd., Jerusalem (IL)

( * ) Notice: Subject to any disclaimer, the term of this patent is extended or adjusted under 35 U.S.C. 154(b) by 0 days.

(21) Appl. No.: 14/218,412

(22) Filed: Mar. 18, 2014

(51) Int. Cl.
*A61M 39/12* (2006.01)
*A61M 39/10* (2006.01)

(52) U.S. Cl.
CPC ....... *A61M 39/12* (2013.01); *A61M 2039/1005* (2013.01); *A61M 2039/1044* (2013.01); *A61M 2039/1077* (2013.01)

(58) Field of Classification Search
CPC ............ A61M 39/10; A61M 39/1011; A61M 2039/1005; A61M 2039/1016; A61M 2039/1022; A61M 2039/1027; A61M 2039/1033; A61M 2039/1038; A61M 2039/1044; A61M 2039/1083; A61M 2039/1094; A61M 39/12; A61M 25/0014; A61M 2039/265
See application file for complete search history.

(56) References Cited

U.S. PATENT DOCUMENTS

| | | | |
|---|---|---|---|
| 6,437,316 B1 * | 8/2002 | Colman et al. | 250/222.1 |
| 6,851,427 B1 * | 2/2005 | Nashed | 128/205.23 |
| 2003/0147597 A1 * | 8/2003 | Duran | 385/76 |
| 2006/0033334 A1 * | 2/2006 | Weber et al. | 285/390 |
| 2008/0265191 A1 | 10/2008 | Walborn | |
| 2011/0315757 A1 * | 12/2011 | Colman et al. | 235/375 |
| 2012/0123392 A1 | 5/2012 | McKinnon | |
| 2012/0169044 A1 * | 7/2012 | Kendrick | 285/313 |
| 2012/0323208 A1 | 12/2012 | Bochenko | |

FOREIGN PATENT DOCUMENTS

| | | |
|---|---|---|
| EP | 0839551 | 5/1998 |
| WO | 2013/088439 | 6/2013 |

OTHER PUBLICATIONS

"Liquid Crystal Displays (LCD)—Working." Circuits Today, Feb. 16, 2013. Web. Apr. 15, 2015. <http://web.archive.org/web/20130216051750/http://www.circuitstoday.com/liquid-crystal-displays-lcd-working>.*

* cited by examiner

*Primary Examiner* — Bhisma Mehta
*Assistant Examiner* — James Ponton
(74) *Attorney, Agent, or Firm* — Rodney J. Fuller; Booth Udall Fuller, PLC (57) ABSTRACT

The present disclosure provides adapters configured to interconnect a device connector of a medical device and a tube connector, the adapter having a first end with a female Luer connector and a second end having a primary Luer male connector, with a secondary female section.

7 Claims, 9 Drawing Sheets

ADAPTERS

TECHNICAL FIELD

The present disclosure generally relates to the field of adapters.

BACKGROUND

Luer Taper is a standardized system of small-scale fluid fittings used for making leak-free connections between a female-taper fitting and its mating male part on medical and laboratory instrument. Key features of Luer connectors are defined in the ISO 594 standards.

The standard Luers are currently being used universally in most medical device categories and applications. However, with the proliferation of medical devices fitted with Luer connectors, and the reports of patient death or injury arising from misconnections, new ISO standard 80369-1 and 80369-2 requiring different connectors for different categories of medical devices was developed.

SUMMARY

The present disclosure relates to adapters, for use in a respiratory gas sampling system, configured to interconnect standard Luer device connectors with connectors confirming with the new ISO 80369-1 and ISO 80369-2 standards.

For the vast majority of connectors the transfer to the new connector standard will mostly affect constituents of the consumable type. However, in the field of breath monitoring systems, the connectors are found on medical devices and systems that have an average life of several years in hospitals and other medical settings and as such present a major barrier to the changeover process. Returning the medical devices to the manufacturer in order to change the device connector is expensive, time consuming and in some cases even infeasible due to the anticipated new, larger, required dimensions.

The adapters disclosed herein, may be configured to interconnect a device connector, such as a standard Luer, of a medical device and a tube connector, conforming to the new ISO standard. The adapters include: a first end having a standard female Luer connector; and a second end having a primary Luer male connector, in the form of a tapered cone, including a secondary female section extending from a top distal part of the primary Luer male connector back towards a proximal part thereof.

Advantageously, the adapters may also include an identification system configured to ensure activation of the medical device only when the tube connector is properly connected to the adapter. This may prevent operation of a medical device when no constituent is connected or even when a correct constituent is improperly connected, thereby reducing damage to sensitive parts of the instrument as well as incorrect readings.

According to some embodiments, the adapters may be configured to be permanently fixed to the medical device. This assures that the purpose of the new standard, i.e. avoiding misconnections of improper constituents to the wrong medical device, is not negated.

Certain embodiments of the present disclosure may include some, all, or none of the above advantages. One or more technical advantages may be readily apparent to those skilled in the art from the figures, descriptions and claims included herein. Moreover, while specific advantages have been enumerated above, various embodiments may include all, some or none of the enumerated advantages.

According to some embodiments, there is provided an adapter configured to interconnect a device connector of a medical device and a tube connector. According to some embodiments, the adapter includes a first end having a female Luer connector, a second end including a primary Luer male connector and at least one light transmitting element. According to some embodiments, the primary Luer male connector has a form of a tapered cone and including a secondary female section extending from a top distal part of the primary Luer male connector back towards a proximal part thereof.

According to some embodiments, the adaptor is configured to ensure activation of said medical device only when the tube connector is properly connected to the adapter.

According to some embodiments, the at least one light transmitting element includes at least one LED positioned on an end face of the first end of the adapter.

According to some embodiments, the adapter further includes an electrical circuit and a power source connected to the electrical circuit, wherein the electrical circuit is normally open, such that no voltage is supplied to the LED and no light emitted therefrom.

According to some embodiments, the primary Luer male connector includes at least two conducting strips positioned on the secondary female section thereof.

According to some embodiments, the tube connector is a female Luer connector having a secondary male section, the secondary male section including a second conductive element configured to close the electrical circuit by closing a circuit with the at least two conducting strips and to ignite the LED, when the tube connector is connected to the adapter. According to some embodiments, the LED is positioned such that light emitted from the LED, can be detected by a connection system of the medical device.

According to some embodiments, the at least one light transmitting element includes a reflective surface. According to some embodiments, light reflected by the reflective surface can be detected by a connection system of the medical device.

According to some embodiments, the adapter includes a liquid crystal display (LCD) positioned in front of the reflective surface on an end face of the first end of the adapter. According to some embodiments, the LCD is normally switched off.

According to some embodiments, the LCD includes parallel polarizers, such that when the LCD is switched off light emitted on the LCD will be blocked from passing therethrough and from reaching the reflective surface.

According to some embodiments, the adapter includes an electrical circuit and a power source connected to the electrical circuit; wherein the electrical circuit is normally open such that no voltage is supplied to the LCD.

According to some embodiments, the primary Luer male connector includes at least two conducting strips positioned on the secondary female section thereof.

According to some embodiments, the tube connector is a female Luer connector having a secondary male section, the secondary male section including a second conductive element configured to close the electrical circuit by closing a circuit with the at least two conductive strips and to switch on the LCD, wherein when the LCD is switched on light emitted on the LCD will pass therethrough and reach the reflective region.

According to some embodiments, the adapter includes a shutter arranged in front of the reflective surface, such that light emitted on the shutter will be blocked from passing therethrough and from reaching the reflective surface.

According to some embodiments, the adapter includes a shaft, arranged such that when the tube connector is connected to the adapter, the shaft will be pushed and the shutter be opened.

According to some embodiments, the at least one light transmitting element includes at least one light transmitting media. According to some embodiments, the light transmitting media is configured to transmit light emitted from the tube connector.

BRIEF DESCRIPTION OF THE DRAWINGS

Examples illustrative of embodiments are described below with reference to figures attached hereto. In the figures, identical structures, elements or parts that appear in more than one figure are generally labeled with a same numeral in all the figures in which they appear. Alternatively, elements or parts that appear in more than one figure may be labeled with different numerals in the different figures in which they appear. Dimensions of components and features shown in the figures are generally chosen for convenience and clarity of presentation and are not necessarily shown in scale. The figures are listed below.

DETAILED DESCRIPTION

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

There is provided, according to some embodiments, an adapter configured to interconnect a male Luer connector, conforming to the ISO 594 standard, and a female Luer connector conforming to the new ISO standards 80369-1 and 80369-2; "Small-bore connectors for liquids and gases in healthcare applications" and "Connectors for breathing systems and driving gases applications", respectively.

According to some embodiments, the Luer connector conforming to the ISO 594 standard is a device connector. As used herein the term "device connector" may refer to an input connector or a socket of a device, such as a medical device.

According to some embodiments, the connector conforming to the new ISO standards 80369-1 and 80369-2 is a tube connector. As used herein the term "tube connector" may refer to the connector molded on or otherwise attached to a constituent, such as but not limited to a breath sampling tube.

As used herein the term "constituent" may refer to cannulas, sampling tubes and any other constituent used in breathing systems. According to some embodiments, the constituent is a breath sampling tube.

According to some embodiments, the adapter includes a first end (device end), for example the end configured to connect with a device connector of a medical device, such as but not limited to a capnograph. According to some embodiments, the first end may include a female Luer connector conforming to the ISO 594 standard (also referred to herein as a standard Luer connector). Alternatively, the first end may include a male Luer connector conforming to the ISO 594 standard.

According to some embodiments, the adapter may further include a second end (tube end) having a primary Luer male connector conforming to the new ISO standards 80369-1 and 80369-2. The primary Luer male connector may have a secondary female section extending from a top distal part of the primary Luer male connector back towards a proximal part thereof. Alternatively, the second end may have a primary Luer female connector conforming to the new ISO standards 80369-1 and 80369-2. The primary Luer female connector may, at its deepest point, invert back into a secondary male section. According to some embodiments, the second end may be configured to connect to a tube connector.

According to some embodiments, the first end of the adapter including a female Luer connector conforming to the ISO 594 standard is smaller than the second end of the adapter including a primary Luer male connector conforming to the new ISO standards 80369-1 and 80369-2. According to some embodiments, the adaptor is cone shaped having a gradually decreasing diameter. Alternatively, the adaptor may include an indentation at the first end thereof accommodating the smaller diameter of the Luer connector conforming to the ISO 594 standard.

According to some embodiments, the primary Luer male connector is configured to connect with a tube connector conforming to the ISO standards 80369-1 and 2. According to some embodiments, the tube connector is a primary Luer female connector having a form of a tapered cone, which at its deepest point, inverts back into a secondary male section (also conforming to the above standard). It is understood to one of ordinary skill in the art that when the primary Luer male connector and the primary Luer female connector mate with each other, the secondary male section is at least partially inserted into the secondary female section.

According to some embodiments, the primary Luer male connector at the second end of the adapter may include an inner fluid flow channel extending along its length from a proximal end thereof to, and in fluid flow connection with, the secondary female section and further to, and in fluid flow connection with, the inner fluid flow channel of the standard Luer female connector at the first end of the adapter. Such configuration of the adapter may facilitate undisturbed flow of breath samples from the breath sampling tube through the connector and further to the medical device for measurements. Hence, the adapter disclosed herein facilitates accurate breath sampling with high waveform fidelity and minimal delays in rise time (time required to achieve a rise from 10% to 90% of the final $CO_2$ concentration).

It is understood to one of ordinary skill in the art that any combination of connectors on the adapter are applicable and as such fall within the scope of the disclosure. For example, the first end may include a standard female Luer connector and the second end a primary Luer male connector with a secondary female section. Alternatively, the first end may include a standard female Luer connector and the second end a primary Luer female connector with a secondary male section. Alternatively, the first end may include a standard male Luer connector and the second end a primary Luer male connector with a secondary female section. Alternatively, the first end may include a standard male Luer connector and the second end a primary Luer female connector with a secondary male section.

According to some embodiments, the adapter is configured to be permanently fixed to the device connector. According to some embodiments, the term "permanently fixed" may refer to an adapter which is provided separately from the device, but once connected is no longer detachable. Alternatively, the term "permanently fixed" may refer to an adapter which is provided separately from the device, but once connected requires a unique procedure to be detached, different from regular attachment/detachment of Luer connectors. According to some embodiments, detachment of the adapter from the device connector may trigger an alarm. It is understood that such essentially permanent attachment of the adapter to the medical device serves to ensure that the guiding principles of safety and prevention of misconnection provided by the new ISO standard 80369-1 and 80369-1 are not compromised.

According to some embodiments, there is provided herein a medical device and adapted configured to interconnect between the device and a sampling tube, such that the device will be activated (turned on) only when the adapter is connected on one end thereof to the device and on another end thereof to the sampling tube. When the adapter is connected only to the device and not to the sampling tube the device will not be activated and will remain turned off.

According to some embodiments, the adapter includes a light transmitting element configured to transmit light (for example, emit, reflect and/or transfer light) to the device detector only when the adapter is connected on one end thereof to the device and on another end thereof to the sampling tube. Thus, the device will only operate upon detection of the transmitted light.

According to some embodiments, the medical device is configured to identify the proper connection of a (sampling) tube connector to the other end of the adapter, using a connection system (herein also referred to as a tube connection system). According to some embodiments, proper connection is identified when a correct tube connector reaches a final position indicating that the connector is entirely inserted into the adapter. According to some embodiments, the medical device is actuated when the connector reaches its final position in the adapter. Additionally or alternatively, according to some embodiments, proper connection is identified when a correct tube connector reaches an intermediate position indicating that the tube connector is partially but sufficiently inserted into the adapter. It is understood by one of ordinary skill in the art that sufficient connection may refer to a connection in which the tube connector is inserted adequately enough into the adapter to avoid leaks and misreadings, but does not necessarily require that the connector reaches its final connection position. According to some embodiments, the medical device is actuated when the connector reaches such intermediate and sufficient connection. In the hospital and emergency environment, the number of tasks required and the limited time available, often create situations where connectors are not mated securely and firmly. Though the user is required to feel the positive feedback received when the fittings are screwed on correctly, the conditions in the medical environment often do not lend themselves for the user to be sensitive to this feedback. This may result in regions of increased diameters as well as leaks thereby negatively influencing readings of the medical device, such as but not limited to capnographic readings. On the other hand, emergency situations may require hasty connection which may be profoundly delayed if complete connection is required. Advantageously, the adapter disclosed herein is configured to facilitate the connection system of the medical device to identify sufficient connection ensuring that the connector is firmly secured in the adapter and that misreadings are avoided while requiring a minimum connection time.

According to some embodiments, the medical device includes at least one light detector, configured to detect light emitted from or otherwise transmitted through the adapter. According to some embodiments, the at least one light detector is configured to detect light of a specific wavelength and/or frequency. According to some embodiments, the at least one detector is configured to only detect light that is transmitted from the tube connector, while light, such as scattered light from the environment, direct light from the light source, and the like, is prevented from reaching the optical detector. According to some embodiments, the connection system may be configured to produce a signal based on the detected light. For example, the connection system may be configured to trigger the actuation of the medical device when a light signal is detected. According to some embodiments, the connection system may further include at least one light source configured to transmit light toward the device end of the adapter. According to some embodiments, the at least one light source is only actuated when a consumable (e.g. a sampling tube) is connected to the adaptor.

According to some embodiments, the adapter may include an identification system configured to identify a proper connection of an appropriate tube connector to the adapter. For example, if the primary Luer female tube connector is not properly connected to the primary Luer male connector of the adapter, or if an improper tube connector is inserted into the primary Luer male connector of the adapter, no signal will be generated by the identification system and as a result, the respiratory gas sampling (such as a capnograph) and/or gas delivery device will not be activated and/or an alert will be produced indicating the improper connection. For this purpose, several methods can be used, for example, a method which is based on identifying changes to an electric circuit by either closing the circuit, changing its inductance or capacitance or the resistance in part of it, etc. Alternatively, a method which is based on detecting optical or magnetic changes can also be applied. Hence, the signal generated by the identification system may be optical, electronic, mechanical or any other suitable signal, as further discussed hereinbelow. Each possibility is a separate embodiment.

According to some embodiments, the adapter (and/or the identification system) may include at least one light transmitting element. According to some embodiments, the light transmitting element may be positioned on an end face of the device end of the adapter. However other configurations enabling light to reach the light detectors of the connection system are also applicable and as such fall under the scope of the present disclosure.

As used herein, the term "light transmitting element" may refer to any element configured to transmit and/or emit light toward the light detectors of the connection system. Non-limiting examples of light transmitting elements include light sources (lamps), reflective surfaces (configured to reflect light impinging thereon back toward the light detectors), light transmitting media (e.g. optical fibers), polarizers, LCDs as well as any other element configured to generate, pass on, or pass therethrough light. Each possibility is a separate embodiment.

According to some embodiments, the light transmitting element includes at least one light source. According to some embodiments, the at least one light source may be a light emitting diode (LED). However, other light sources or lamps are also applicable and as such covered by the scope of the present disclosure. According to some embodiments, the at least one light source is arranged such that light emitted from the light source can be detected by a connection system of the medical device. As a non-limiting example, the at least one light source may be positioned on an end face of the first end (device end) of the adapter. As used herein, the term at least one light source may refer to 1, 2, 3, 4, 5 or more light sources. Each possibility is a separate embodiment.

According to some embodiment, the adapter may further include an electrical circuit connected to the at least one light source. According to some embodiments, the adapter may further include a power source connected to the electrical circuit and configured to provide voltage to the at least one light source. According to some embodiments, the power source may be located in proximity to the light transmitting element, however other configurations are likewise applicable.

According to some embodiments, the electrical circuit is normally open, such that no voltage is supplied to the at least one light source and no light emitted therefrom.

According to some embodiments, the primary Luer male connector of the adapter may, optionally on the secondary female section thereof, include at least two first conducting elements arranged such that the electrical circuit remains open unless an additional conductive element is introduced into the circuit. For example, the circuit may be closed when a female Luer tube connector having a second conducting element, optionally positioned on the secondary male section, is properly connected to the adapter. According to some embodiments, the at least two first conducting elements at least two conductive strips located, for example, on the side walls of the secondary female section. According to some embodiments the at least two conductive elements are molded on, embedded in or otherwise attached to the secondary female section.

According to some embodiments, the second conducting element of the tube connector may be a conducting ring located on an outer circumference of the secondary male section. Alternatively, the second conducting element may be at least one conductive strip located, for example, on outer walls or on an end face of the secondary female section. According to some embodiments the conductive element is molded on, embedded in or otherwise attached to the secondary female section. According to some embodiments, the entire secondary male section, or parts thereof, may be conductive. For example, the secondary female section of the tube connector may be formed of a conductive material. According to some embodiments, the conductive element may thus be an integral part of secondary female section or parts thereof.

According to some embodiments, when a female Luer tube connector having a second conducting element is connected to the primary Luer male connector of the adapter, the electrical circuit is closed and thus voltage is supplied to at least one light source. The light emitted from the light source can be detected by the connection system of the medical device which may consequently be turned on.

According to some embodiments, the second end of the adaptor (the tube end) may have a cover configured to cover the primary Luer male connector or parts thereof, when no tube connecter is connected to the adapter. As used herein the term "cover" may refer to any element configured to cover the tube end of the adapter when no tube connector is connected. Non-limiting examples of suitable covers include door, curtains, flaps as well as other suitable elements. According to some embodiments, the cover may be spring loaded such that it automatically covers the inlet of the second connector when no tube connector is connected to the adaptor.

According to some embodiments, the cover may include a conducting element. According to some embodiments, the cover may be arranged such that in order to connect a tube connector to the adapter, the cover must be turned or otherwise moved away from the inlet of the second connector of the adapter. According to some embodiments, when a female Luer tube connector is connected to the primary Luer male connector of the adapter, the conductive element on the cover closes the electrical circuit and voltage is supplied to at least one light source. The light emitted from the light source can be detected by the connection system of the medical device which may consequently be turned on.

It is understood by one of ordinary skill in the art that these configurations of the adapter may be utilized to ensure, that when no tube connector and hence no constituent is attached to the adapter, the electrical circuit remains open and no light is emitted from the at least one light source. Accordingly, no light signal is detected by the tube connection system and the medical device is not actuated. This may ensure that on the one hand unnecessary wear of the medical device is avoided and on the other hand unnecessary and environmentally harmful waste of energy due to the excessive activation of the medical device is reduced.

It is further clear, that when no tube connector is connected to the adapter, the identification system itself is in a 'power save' mode, as the electrical circuit is open and the at least one light source is turned off. Accordingly, the identification system is likewise configured to operate in a power saving and environmentally safe manner.

According to some embodiments, the adapter (and/or the identification system) may include a light transmitting element having a reflective surface. According to some embodiments, the reflective surface may be configured to reflect light transmitted from at least one light source of the medical device. According to some embodiments, the reflective surface may be arranged such that light emitted from the reflective surface can be detected by the connection system of the medical device. As a non-limiting example, the reflective surface may be positioned on an end face of the first end (device end) of the adapter. According to some embodiment the reflective surface may be molded on, embedded in or otherwise attached to the end face. According to some embodiment the reflective surface may cover the entire end face of the device end of the adapter. Alternatively, the reflective surface may cover part of the end face. According to some embodiments, the reflective surface may include more than one reflective element, such as 2, 3, 4 or more reflective elements disposed at different circumferential positions of the end face.

According to some embodiments, the adapter may include a liquid crystal display (LCD). According to some embodiments, LCD may be positioned in front of the reflective surface. As used herein the term "in front of" may refer to a configuration where the reflective surface is positioned on the first end (device end) of the adapter and the LCD externally thereto, such that the reflective surface is located between the end face of the adapter and the LCD. According to some embodiment, the LCD and the reflective surface may be located on an end face of the first end of the adapter in such way that the LCD is positioned externally to the reflective surface and nearer the device connecter. However, other configuration which enable the establishment of an optical path between the connection system of the medical device and the LCD and the reflective surface are also applicable and as such fall under the scope of this disclosure.

According to some embodiments, the LCD may include a layer of liquid-crystal molecules aligned between two polarizing filters, the axes of transmission of which may be parallel or perpendicular to each other. When no voltage is applied, the liquid crystal between the polarizing filters is arranged such that the polarization direction of the light impinging thereon is switched, such that light exiting the liquid crystal will have a polarization direction perpendicular to the polarization direction of the incident light. Hence, light transmitted (for example from the at least one light source of the medical device) will pass the first polarizer as polarized light, change its polarization direction in the crystalline material before reaching the second polarizer.

According to some embodiments, the LCD may include parallel polarizers, such that when the LCD is switched off and no voltage is supplied, light emitted on the LCD will be blocked from passing the second (parallel) polarizer and therefore from reaching the reflective surface. Alternatively, the LCD may include perpendicular polarizers, such that when the LCD is switched off and no voltage is supplied, light emitted on the LCD will pass the first polarizer with a first polarization direction, exit the liquid crystal with a second polarization direction, essentially perpendicular to the first polarization, enabling it to pass the second polarizing element and thus be reflected by the reflective surface.

According to some embodiment, the adapter may further include an electrical circuit connected to the LCD. According to some embodiments, the adapter may further include a power source connected to the electrical circuit and configured to provide voltage to the at least one light source.

According to some embodiments, the electrical circuit may be normally open, such that no voltage is supplied to the LCD. However, in some alternative configurations the electrical surface may be normally closed.

According to some embodiments, the primary Luer male connector of the adapter may, optionally on the secondary female section thereof, include at least two first conducting elements arranged such that the electrical circuit remains open unless an additional conductive element is introduced into the circuit. For example, the circuit may be closed when a female Luer tube connector having a second conducting element, optionally positioned on the secondary male section, is properly connected to the adapter, as essentially described above.

According to some embodiments, when a female Luer tube connector having a second conducting element is connected to the primary Luer male connector of the adapter, the electrical circuit is closed and thus voltage is supplied to the LCD.

As a result thereof, the orientation of the liquid crystal is altered, such that the polarization of the incident light (light emitted from the light source and passed through the first polarizer) is no longer rotated as it proceeds through the liquid crystal layer. According to some embodiments, when the LCD includes parallel polarizers, light emitted on the ignited LCD will be able to pass both parallel polarizers and be reflected by the reflective surface. The reflected light can then be detected by the connection system of the medical device which may consequently be turned on.

According to some embodiments, the second end of the adaptor (the tube end) may have a cover configured to cover the primary Luer male connector or parts thereof, when no tube connecter is connected to the adapter, as essentially described above. According to some embodiments, when a female Luer tube connector is connected to the primary Luer male connector of the adapter, the conductive element on the cover closes the electrical circuit and voltage is supplied to the LCD. Light emitted on the ignited LCD will then be able to pass the LCD and be reflected by the reflective surface. The reflected light can then be detected by the connection system of the medical device which may consequently be turned on.

It is understood by one of ordinary skill in the art that these configurations may be utilized to ensure, that when no tube connector and hence no constituent is attached to the adapter, the electrical circuit remains open, no voltage is supplied to the LCD and therefore, light emitted on the LCD will be blocked from passing therethrough and from reaching the reflective surface. As no light is emitted from the reflective surface, no signal is detected by the tube connection system and the medical device is not actuated. This may ensure that on the one hand unnecessary wear of the medical device is avoided and on the other hand unnecessary and environmentally harmful waste of energy due to the excessive activation of the medical device is reduced.

It is further clear, that when no tube connector is connected to the adapter, the identification system itself is in a 'power save' mode, as the electrical circuit is open and the LCD is turned off. Accordingly, the identification system is likewise configured to operate in a power saving and environmentally safe manner.

According to some embodiments, the adapter may include a shutter arranged in front of the reflective surface, such that light emitted on the shutter will be blocked from passing therethrough and from reaching the reflective surface. As used herein, the term "in front of" may refer to a configuration where the reflective surface is positioned on the first end (device end) of the adapter and the shutter externally thereto. According to some embodiments, the shutter and the reflective surface may be located on an end face of the first end of the adapter in such way that the shutter is positioned externally to the reflective surface and nearer the device connecter. However, other configuration which enable the establishment of an optical path between the connection system of the medical device and the shutter and the reflective surface are also applicable and as such fall under the scope of this disclosure.

According to some embodiments, the adapter may further include a shaft, arranged such that when the tube connector is connected to the adapter, the shaft will be pushed and the shutter be opened. According to some embodiments, the term "shaft" may refer to any element configured to open the shutter. According to some embodiments, the shaft may be replaced by a pushbutton a, a flex sensor, a spring or any other suitable element configured to switch its position, configuration or any other suitable property (e.g. resistance) and as a consequence thereof, open the shutter. Each possibility is a separate embodiment.

According to some embodiments, when light emitted from the at least one light source of the medical device is transmitted toward the reflective surface, when no tube connector is attached, the shutter will block the light from reaching the reflective surface and thus no light is reflected. However, when a tube connector is connecter is connected to the adapter, it may push the shaft thereby opening the shutter. Light emitted from the at least one light source of the medical device may now reach the reflective surface, be reflected therefrom and consequently be detected by the connection system.

According to some embodiments, the tube connector may optionally include a protrusion configured to push on the shaft when the tube connector is properly connected to the adapter.

According to some embodiments, the second end of the adaptor (the tube end) may have a cover configured to cover the primary Luer male connector or parts thereof, when no tube connecter is connected to the adapter. According to some embodiments, the cover may be spring loaded such that it automatically covers the inlet of the second connector when no tube connector is connected to the adaptor.

According to some embodiments, the cover may be arranged such that in order to connect a tube connector to the adapter, the cover must be turned or otherwise moved away from the inlet of the second connector of the adapter. According to some embodiments, when a female Luer tube connector is connected to the primary Luer male connector of the adapter, the cover pushes on the shaft (or on the pushbutton) and consequently opens the shutter. Light emitted from the at least one light source of the medical device may consequently reach the reflective surface, be reflected therefrom and thus be detected by the connection system.

According to some embodiments, the adapter (and/or the identification system) may include a light transmitting element having at least one light transmitting media configured to transmit light emitted from a tube connector, connected to the adapter, to the device connector, and consequently to the connection system of the medical device.

According to some embodiments, the at least one transmitting media may include 1, 2, 3, 4 or more transmitting media. Each possibility is a separate embodiment.

According to some embodiments, the at least one transmitting media may be light pipes, optical fibers, reflective coated cavities or any other suitable light transmitting media.

According to some embodiments, the tube connector includes a reflective surface. According to some embodiments light emitted from the at least one light source of the medical device may be transmitted by the transmitting media to the reflective surface of the tube connector. The light reflected by the reflective surface of the tube connector may then be transmitted by the transmitting media to the light detector of the connection system.

According to some embodiments, the tube connector includes a light source such as but not limited to a LED. According to some embodiments light emitted by the LED may be transmitted by the transmitting media to the light detector of the connection system.

According to some embodiments, the adapter may include a reflective surface and a spring loaded insert configured to push the reflective surface closer to the light detector of the connection system when a tube connector is connected to the adapter. According to some embodiments, when no tube connector is connected to the adaptor light emitted from the at least one light source of the medical device may not reach the reflective surface. Additionally or alternatively, when no tube connector is connected to the adaptor, light emitted by the reflective surface will not reach the light detector of the connection system. According to some embodiments, when a tube connector is connected to the adaptor, the spring loaded insert will push the reflective surface sufficiently close to the light detector of the connection system for the reflected light to be detected.

According to some embodiments, the adapter may include a light source and a spring loaded insert configured to push the light source closer to the light detector of the connection system when a tube connector is connected to the adapter. According to some embodiments, when no tube connector is connected to the adaptor, light emitted by the light source of the adapter will not reach the light detector of the connection system. According to some embodiments, when a tube connector is connected to the adaptor, the spring loaded insert will push the light source sufficiently close to the light detector of the connection system for the light emitted thereby to be detected.

The principles, uses and implementations of the teachings herein may be better understood with reference to the accompanying description and figures. Upon perusal of the description and figures present herein, one skilled in the art is able to implement the teachings without undue effort or experimentation.

Before explaining at least one embodiment in detail, it is to be understood that aspects of the embodiments are not necessarily limited in their application to the details of construction and the arrangement of the components and/or methods set forth herein. Some embodiments may be practiced or carried out in various ways. The phraseology and terminology employed herein are for descriptive purpose and should not be regarded as limiting.

Figure 1A:
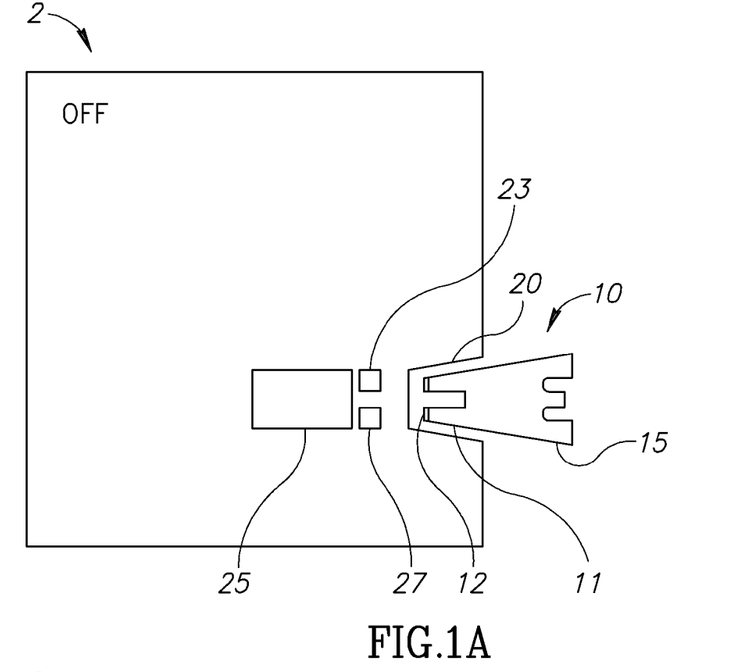
FIG. 1A schematically illustrates an adaptor connected to a medical device, according to some embodiments.
Figure 1B:
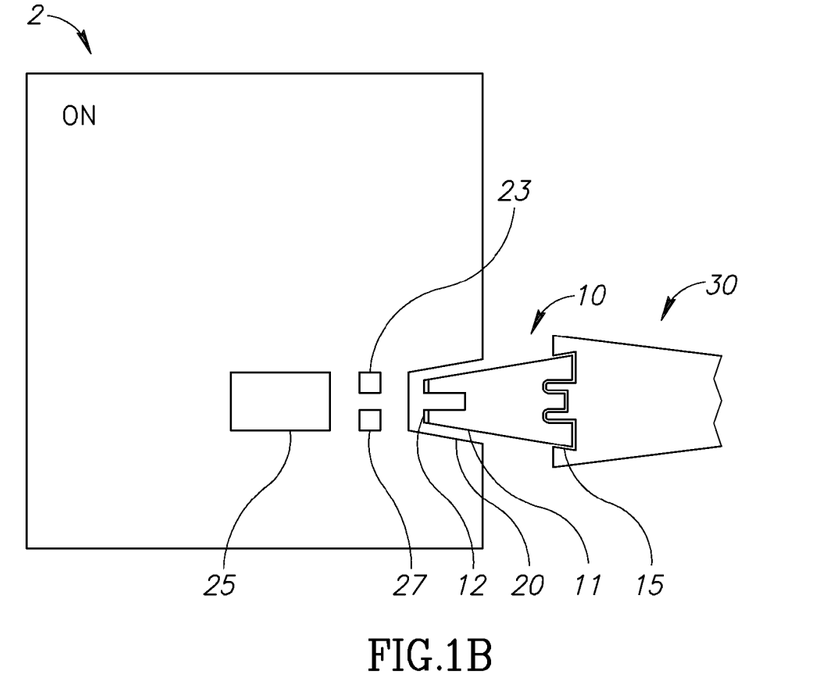
FIG. 1B schematically illustrates an adaptor connected to a medical device and a sampling tube, according to some embodiments.

Reference is now made to FIGS. 1A and 1B, which schematically illustrate an adapter connected to a medical device only or to medical device and a sampling tube, respectively.

Medical device 2 includes a device connector 20, conforming to the ISO 594 standard, a connection system 25, a light detector 27 and optionally a light source, such as light source 23. Adaptor 10 has a female Luer connector 11, conforming to the ISO 594 standard and configured to connect to device connector 20; and a primary Luer male connector 15 conforming to the new ISO 80369-1 and ISO 80369-2 standards and configured to connect to a tube connector 30 (FIG. 1B). Adaptor 10 further includes a light transmitting element 12, according to any of the embodiments described herein and configured to ensure activation of medical device 2 only when tube connector 30 (and hence a tube or other constituent) is attached to adapter 10. When no tube connector is connected to adapter 10, as in FIG. 1A, light transmitting element 12 will not transmit light toward light detector 27 and medical device 2 will remain unactuated. When tube connector 30 is connected to adapter 10, as in FIG. 1B, light transmitting element 12 will transmit light toward light detector 27, and medical device 2 will be actuated.

Figure 2A:
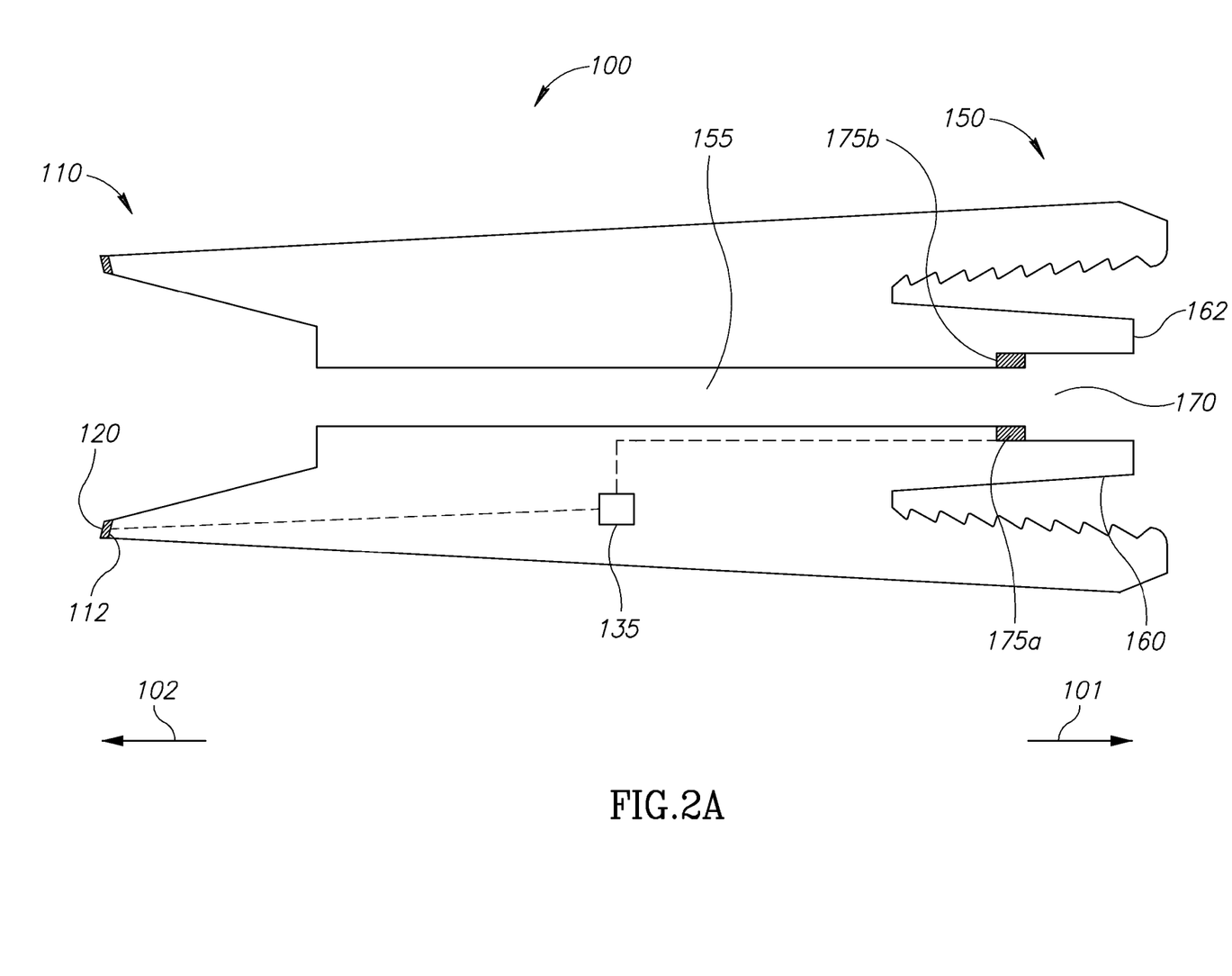
FIG. 2A schematically illustrates an adapter comprising a light source, according to some embodiments.

Reference is now made to FIG. 2A, which schematically illustrates an adapter 100, according to some embodiments. Adapter 100 includes a first end 101 (also termed the tube end), configured to be connected to a tube connector, conforming with the new ISO 80369-1 and ISO 80369-2 standards, such as but not limited to a tube connector of a breath sampling tube (not shown); and a second end 102 (also termed the device end), configured to be connected to a device connector, conforming to the ISO 594 standard, such as but not limited to a device connector of a capnograph (not shown). Device end 102 includes a female Luer connector 110, conforming to the ISO 594 standard. Tube end 101 includes a connector 150 conforming to the new ISO 80369-1 and ISO 80369-2 standards. Connector 150 includes a primary Luer male connector 160, having a form of a tapered cone. Primary Luer male connector 160 has a secondary female section 170, extending from a top distal part 162 of primary Luer male connector 160 back towards a proximal part thereof. Adapter 100 further includes a (centralized) inner fluid flow channel 155 extending along the length of adapter 100.

Adapter 100 includes a light source 120, such as but not limited to a LED. Light source 120 is positioned on an end face 112 (covering part of or the entire end face 112) of female Luer connector 110. However, other configurations enabling an optical path between light source 120 and a connection system (not shown) including one or more light detectors configured to detect light emitted from light source 120 are also applicable and as such fall under the scope of this disclosure. Light source 120 is a part of a normally open electrical circuit, such that when no tube connector is attached to adapter 100, light source 120 is turned off. Adapter 100 further includes a power source 135 connected to the electrical circuit and configured to provide voltage to light source 120.

Adapter 100 further includes two conducting elements 175a and 175b (here conducting strips positioned on secondary female section 170 of primary Luer male connector 160). According to some embodiments, conducting elements 175a and 175b are positioned on the inner circumference of secondary female section 170. However, other configurations are also applicable and as such fall under the scope of the disclosure. Conducting elements 175a and 175b are arranged such that when no tube connector is connected to adapter 100, the electrical circuit is open and only introduction of an additional conducting element will close the electrical circuit and thereby turn on light source 120, as further explained hereinbelow.

Figure 2B:
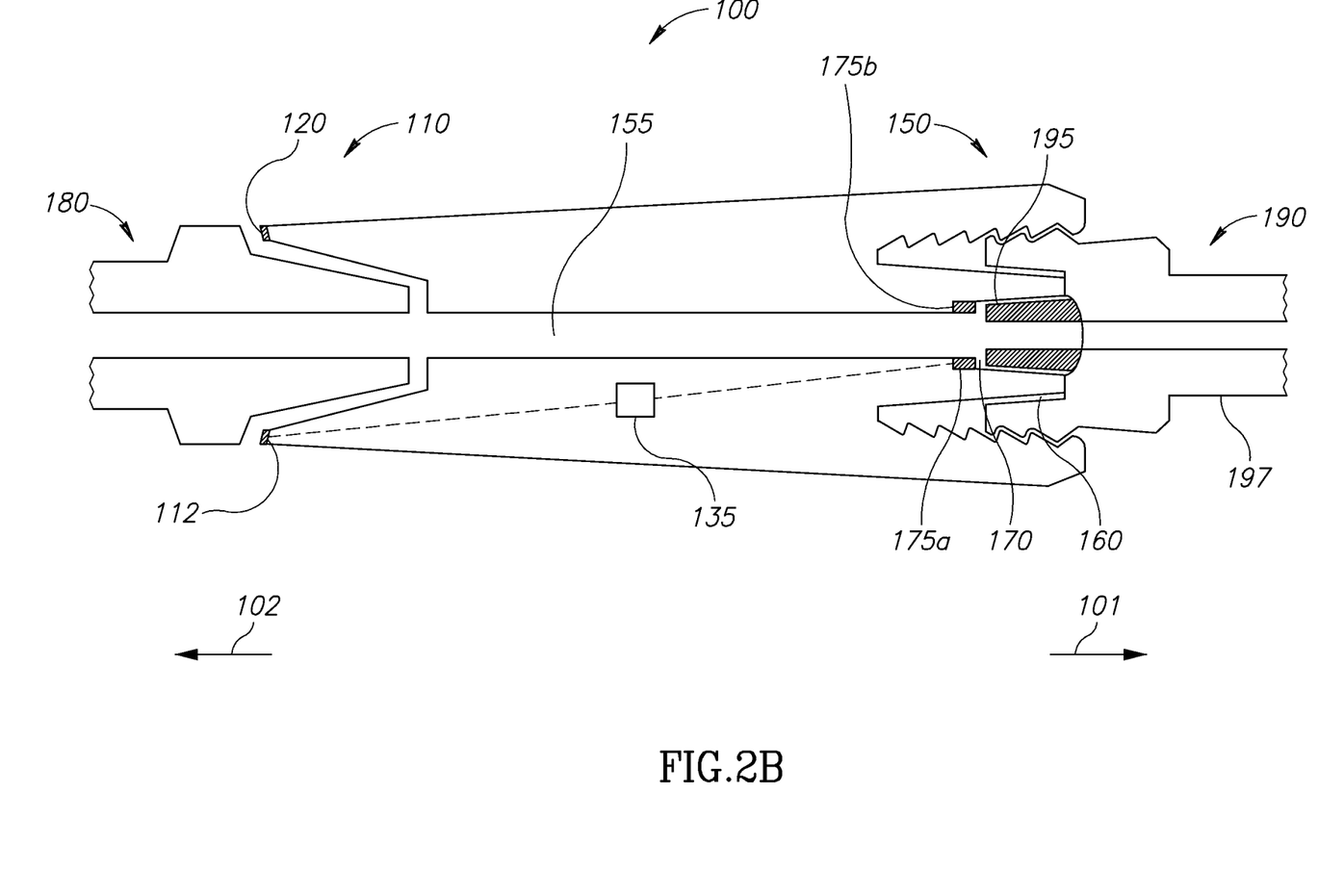
FIG. 2B schematically illustrates the adapter of FIG. 2A, interconnecting between a device connector conforming to ISO 594 and a tube connector conforming to ISO standard 80369-1 and ISO 80369-2, according to some embodiments.

Reference is now made to FIG. 2B, which schematically illustrates adapter 100, as described in FIG. 2A, interconnecting between a standard Luer device connector 180, conforming to the ISO 594 standard, and a tube connector 190 conforming to the ISO 80369-1 and ISO 80369-2 standards.

Adapter 100 includes a first end 101 (also termed the tube end), configured to be connected to tube connector 190, conforming with the new ISO 80369-1 and ISO 80369-2 standards, and a second end 102 (also termed the device end), configured to be connected to device connector 180, conforming to the ISO 594 standard. Device end 102 of adapter 100 includes a female Luer connector 110, conforming to the ISO 594 standard; and tube end 101 includes a connector 150 conforming to the new ISO 80369-1 and ISO 80369-2 standards. Connector 150 includes primary Luer male connector 160, and secondary female section 170. Adapter 100 further includes a (centralized) inner fluid flow channel 155 extending along its length of adapter 100. Thus, exhaled breath can enter first end 101 of adapter 100, through connector 150 connected to a breath sampling tube 197 via tube connector 190. In adapter 100 breath can continue its flow through inner fluid flow channel 155 to the medical device (e.g. the capnograph) through device connector 180 connected to female Luer connector 110. It is understood by one of ordinary skill in the art that only minor changes in diameter are incurred in the flow path of breath through adapter 100 and interconnected tube connector 190 and device connector 180, such that negative effects on the rise time are largely avoided.

Adapter 100 includes a light source 120, such as but not limited to a LED. Light source 120 is positioned on an end face 112 (covering part of or the entire end face 112) of female Luer connector 110. However, other configurations enabling an optical path between light source 120 and a connection system (not shown) including one or more light detectors configured to detect light emitted from light source 120 are also applicable and as such fall under the scope of this disclosure. Light source 120 is a part of a normally open electrical circuit, such that when no tube connector is attached to adapter 100, light source 120 is turned off. Adapter 100 further includes a power source 135 connected to the electrical circuit and configured to provide voltage to light source 120.

Adapter 100 further includes two conducting elements 175a and 175b (here two conducting strips positioned on secondary female section 170 of primary Luer male connector 160). According to some embodiments, conducting elements 175a and 175b are positioned on the inner circumference of secondary female section 170. However, other configurations are also applicable and as such fall under the scope of the disclosure. Conducting elements 175a and 175b are arranged such that when tube connector 190 having a conductive secondary male section 195 (or having a second conductive element disposed thereon) is sufficiently inserted into adapter 100, conductive secondary male section 195 closes a circuit with conducting elements 175a and 175b thereby turning on light source 120. The emitted light may then be detected by a tube connection system of the medical device (not shown) and in effect trigger actuation of the medical device.

It is understood that conducting elements 175a and 175b are arranged such that if tube connector 190 is not adequately inserted into adapter 100 thus increasing the risk of disconnection and misreadings, conductive secondary male section 195 does not close a circuit with conducting elements 175a and 175b. In effect light source 120 remains turned off and the medical device is not actuated. However, according to some embodiments, complete connection may not be required.

Figure 3A:
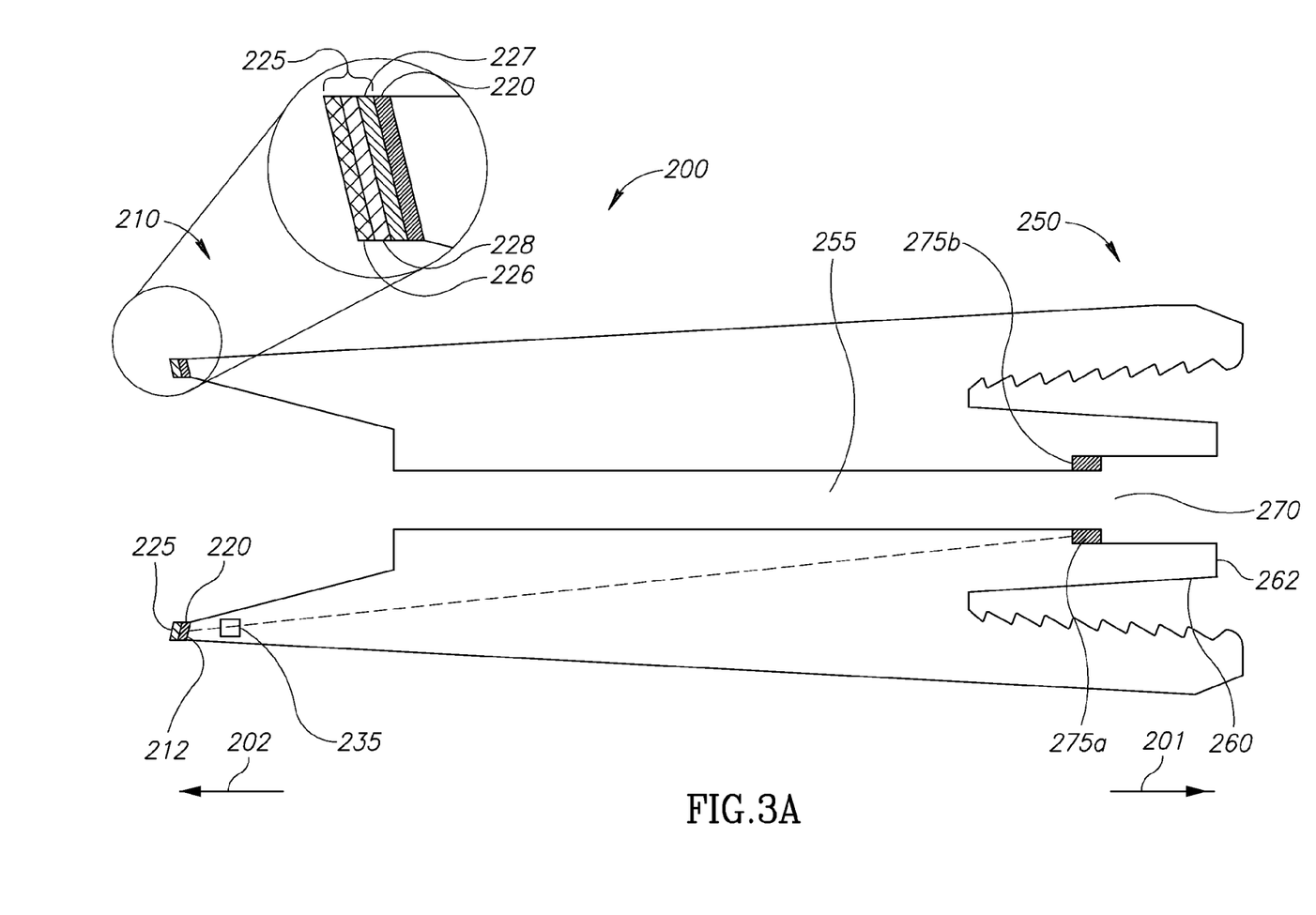
FIG. 3A schematically illustrates an adapter comprising a reflective surface and a liquid crystal display (LCD), according to some embodiments.

Reference is now made to FIG. 3A, which schematically illustrates an adapter 200, according to some embodiments. Adapter 200 includes a first end 201 (also termed the tube end), configured to be connected to a tube connector, conforming with the new ISO 80369-1 and ISO 80369-2 standards, such as but not limited to a tube connector of a breath sampling tube (not shown); and a second end 202 (also termed the device end), configured to be connected to a device connector, conforming to the ISO 594 standard, such as but not limited to a device connector of a capnograph (not shown). Device end 202 includes a female Luer connector 210, conforming to the ISO 594 standard. Tube end 201 includes a connector 250 conforming to the new ISO 80369-1 and ISO 80369-2 standards. Connector 250 includes a primary Luer male connector 260, having a form of a tapered cone. Primary Luer male connector 260 has a secondary female section 270, extending from a top distal part 262 of primary Luer male connector 260 back towards a proximal part thereof. Adapter 200 further includes a (centralized) inner fluid flow channel 255 extending along the length of adapter 200.

Adapter 200 includes a reflective surface 220. Reflective surface 220 is positioned on an end face 212 of female Luer connector 210 (covering part or the entire of end face 212). However, other configurations enabling an optical path between reflective surface 220 and a connection system (not shown) including one or more light detectors configured to detect light reflected from reflective surface 220 are also applicable and as such fall under the scope of this disclosure. Adapter 200 further includes a liquid crystal display (LCD) 225 having two parallel polarizers, first polarizer 226 and second polarizer 227, on opposite sides of crystalline material 228. LCD 225 is positioned externally to reflective surface 220 (proximal to device end 202) on end face 212. LCD 225 is part of a normally open electrical circuit, such that when no tube connector is attached to adapter 200, LCD 225 is turned off. Adapter 200 further includes a power source 235 connected to the electrical circuit and configured to provide voltage to LCD 225.

Adapter 200 further includes a conducting element 275a and 275b (here two conducting strips positioned on secondary female section 270 of primary Luer male connector 260). According to some embodiments, conducting element 275a and 275b are positioned on the inner circumference of secondary female section 270. However, other configurations are also applicable and as such fall under the scope of the disclosure. Conducting elements 275a and 275b are arranged such that when no tube connector is connected to adapter 200, the electrical circuit is open and only introduction of an additional conducting element will close the electrical circuit and consequently turn on LCD 225, as further explained hereinbelow.

Figure 3B:
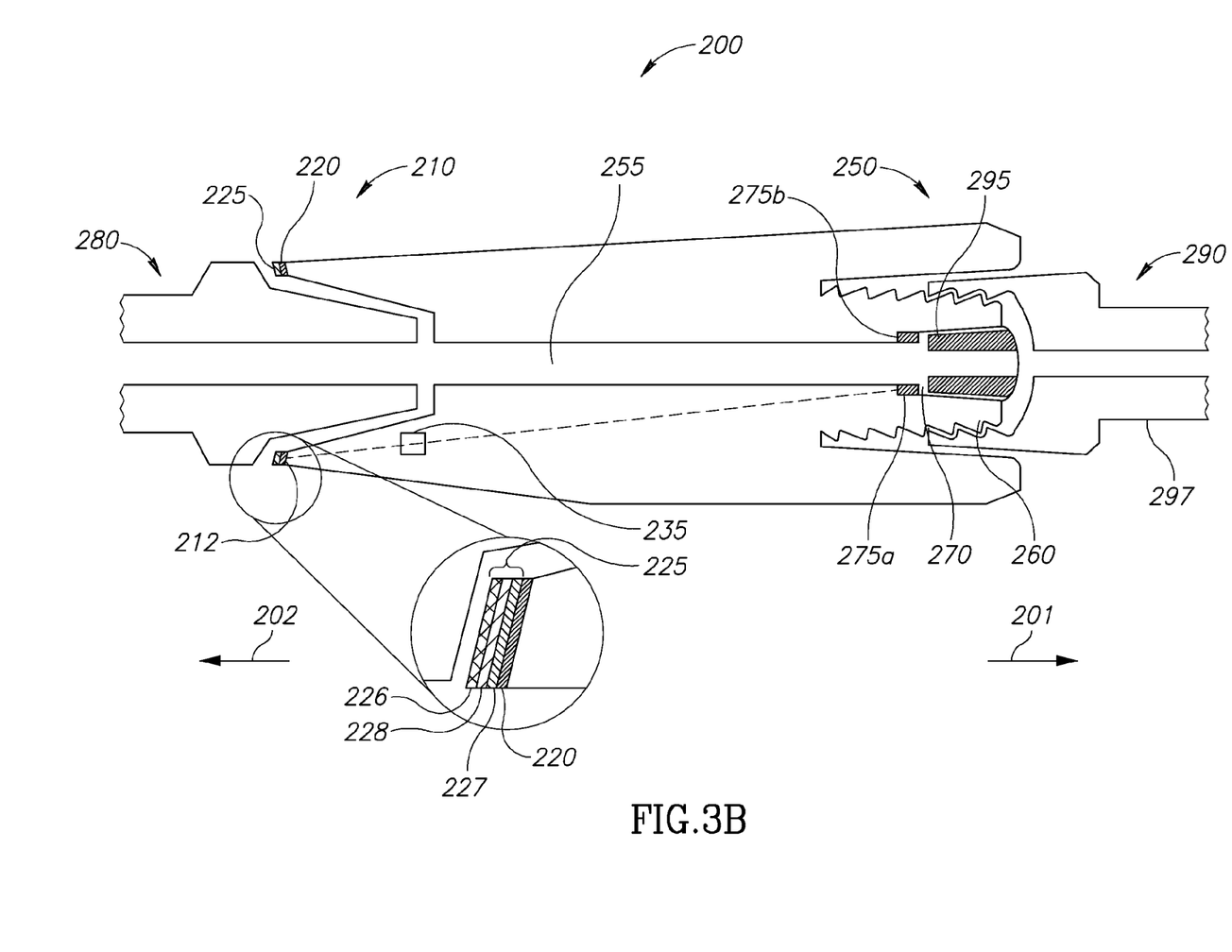
FIG. 3B schematically illustrates the adapter of FIG. 3A, interconnecting between a device connector conforming to ISO 594 and a tube connector conforming to ISO standard 80369-1, according to some embodiments.

Reference is now made to FIG. 3B, which schematically illustrates adapter 200, as described in FIG. 3A, interconnecting between a Luer device connector 280, conforming to the ISO 594 standard, and a tube connector 290 conforming to the ISO 80369-1 and ISO 80369-2 standards.

Adapter 200 includes a first end 201 (also termed the tube end), configured to be connected to tube connector 290, conforming with the new ISO 80369-1 and ISO 80369-2 standards, and a second end 202 (also termed the device end), configured to be connected to device connector 280, conforming to the ISO 594 standard. Device end 202 of adapter 200 includes a female Luer connector 210, conforming to the ISO 594 standard and tube end 201 includes a connector 250 conforming to the new ISO 80369-1 and ISO 80369-2 standards. Connector 250 includes primary Luer male connector 260, and secondary female section 270. Adapter 200 further includes a (centralized) inner fluid flow channel 255 extending along the length of adapter 200. Thus, exhaled breath can enter first end 201 of adapter 200, through connector 250 connected to a breath sampling tube 297 via tube connector 290. In adapter 200 breath can continue its flow through inner fluid flow channel 255 and to the medical device (e.g. the capnograph) through device connector 280 connected to female Luer connector 210. It is understood by one of ordinary skill in the art that only minor changes in diameter are incurred in the flow path of breath through adapter 200 and interconnected tube connector 290 and device connector 280, such that negative effects on the rise time are largely avoided.

Adapter 200 includes a reflective surface 220. Reflective surface 220 is positioned on an end face 212 (covering part of or the entire end face 212) of female Luer connector 210. However, other configurations enabling an optical path between reflective surface 220 and a connection (not shown) system including one or more light detectors configured to detect light reflected from reflective surface 220 are also applicable and as such fall under the scope of this disclosure. Adapter 200 further includes a liquid crystal display (LCD) 225 having parallel polarizers and being positioned externally to reflective surface 220 (proximal to device end 202) on end face 212 (or parts thereof). LCD 225 is part of a normally open electrical circuit, such that when no tube connector is attached to adapter 200, LCD 225 is turned off. Adapter 200 further includes a power source 235 connected to the electrical circuit and configured to provide voltage to LCD 225.

In effect, light impinging on end face 212 (by one or more light sources of the medical device) will be blocked by LCD 225 having two parallel polarizers, first polarizer 226 and second polarizer 227, on opposite sides of crystalline material 228. This since crystalline material 228 of LCD 225 will change the polarization direction of the impinging light of a first polarization direction, acquired when passing through first polarizer 226 of LCD 225, to a second polarization direction essentially perpendicular to the first polarization. Light having the second polarization direction will now be blocked by second polarizer 227, parallel to first polarizer 226, and will therefore not reach reflective surface 220.

Adapter 200 further includes two conducting elements 275a and 275b (here two conducting strips) positioned on secondary female section 270 of primary Luer male connector 260. According to some embodiments, conducting elements 275a and 275b are positioned on the inner circumference of secondary female section 270. However, other configurations are also applicable and as such fall under the scope of the disclosure. Conducting elements 275a and 275b are arranged such that when tube connector 290 having a conductive secondary male section 295 (or having a second conductive element disposed thereon) is sufficiently inserted into adapter 200, conductive secondary male section 295 closes a circuit with conducting elements 275a and 275b thereby turning on LCD 225. In effect, light impinging on end face 212 (by one or more light sources of the medical device) will no longer be blocked by LCD 225 having parallel polarizers, 226 and 227, on opposite sides of crystalline material 228, since when voltage is supplied to LCD 225 crystalline material 228 is rearranged such that the polarization direction of light passing through crystalline material 228 remains unchanged. Light passing first polarizer 226 will therefore maintain its polarization direction when passing through crystalline material 228 and will thus be able to pass through second polarizer 227 and reach reflective surface 220. Light reflected from reflective surface 220 can then be detected by a tube connection system of the medical device (not shown) and in effect trigger actuation of the medical device.

It is understood that conducting elements 275a and 275b are arranged such that if tube connector 290 is not adequately inserted into adapter 200 thus increasing the risk of disconnection and misreadings, conductive secondary male section 295 does not close a circuit with conducting elements 275a and 275b. In effect LCD 225 remains turned off and the medical device is not actuated. However, according to some embodiments, complete connection may not be required.

Figure 4A:
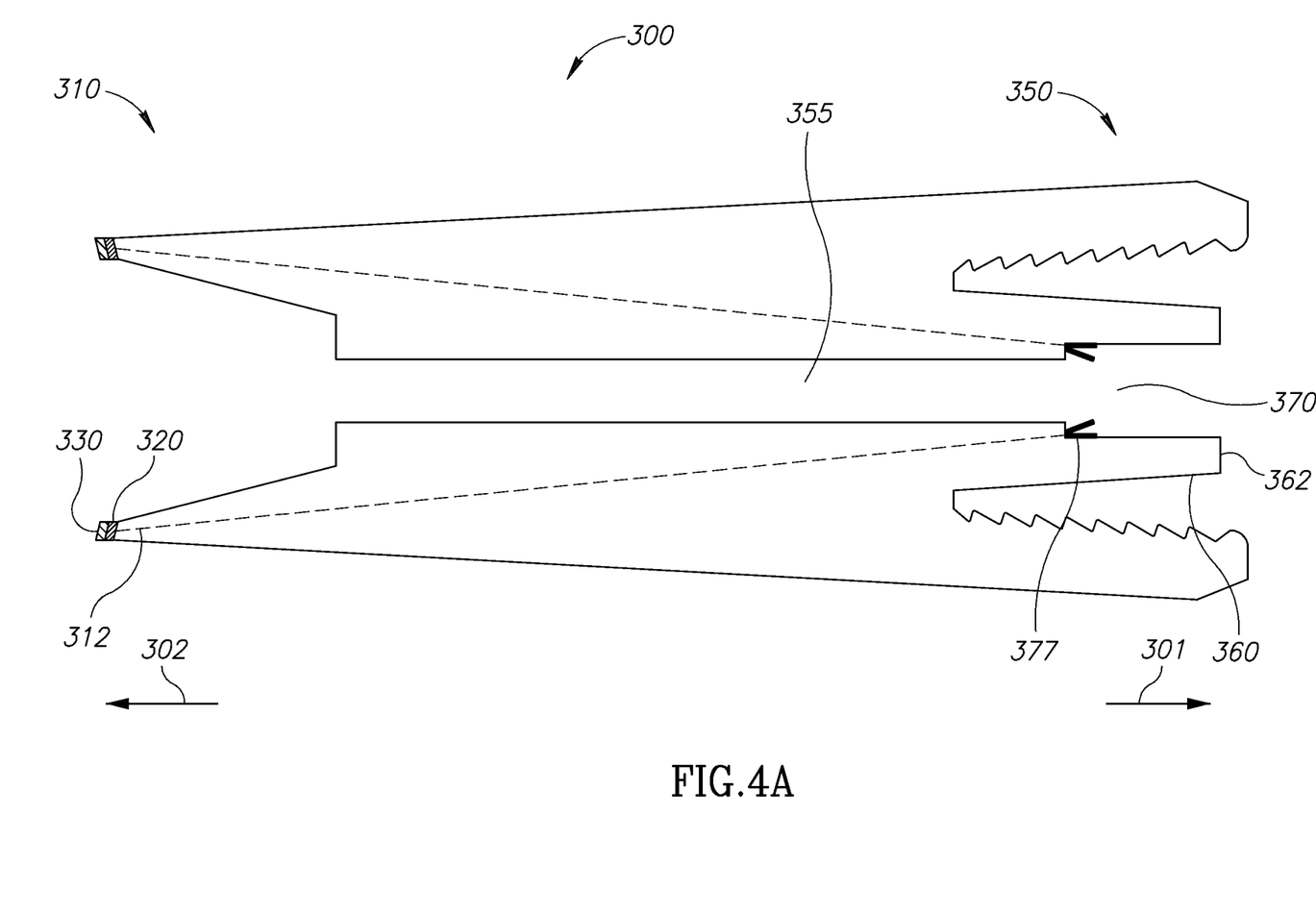
FIG. 4A schematically illustrates an adapter comprising a reflective surface and a shutter, according to some embodiments.

Reference is now made to FIG. 4A, which schematically illustrates an adapter 300, according to some embodiments. Adapter 300 includes a first end 301 (also termed the tube end), configured to be connected to a tube connector, conforming with the new ISO 80369-1 and ISO 80369-2 standards, such as but not limited to a tube connector of a breath sampling tube (not shown); and a second end 302 (also termed the device end), configured to be connected to a device connector, conforming to the ISO 594 standard, such as but not limited to a device connector of a capnograph (not shown). Device end 302 includes a female Luer connector 310, conforming to the ISO 594 standard. Tube end 301 includes a connector 350 conforming to the new ISO 80369-1 and ISO 80369-2 standards. Connector 350 includes a primary Luer male connector 360, having a form of a tapered cone. Primary Luer male connector 360 has a secondary female section 370, extending from a top distal part 362 of primary Luer male connector 360 back towards a proximal part thereof. Adapter 300 further includes a (centralized) inner fluid flow channel 355 extending along the length of adapter 300.

Adapter 300 includes a reflective surface 320. Reflective surface 320 is positioned on an end face 312 (covering part of or the entire end face 312) of female Luer connector 310. However, other configurations enabling an optical path between reflective surface 320 and a connection system (not shown) including one or more light detectors configured to detect light reflected from reflective surface 320 are also applicable and as such fall under the scope of this disclosure. Adapter 300 further includes a shutter 330 positioned externally to reflective surface 320 (proximal to device end 302) on end face 312 (or parts thereof). Shutter 330 is normally closed, such that when no tube connector is attached to adapter 300, light emitted on shutter 330 (by one or more light sources of the medical device) will be blocked from passing therethrough and from reaching reflective surface 320.

Adapter 300 further includes a shaft 377 (here positioned on secondary female section 370 of primary Luer male connector 360). According to some embodiments, shaft 377 is positioned on the inner circumference of secondary female section 370. However, other configurations are also applicable and as such fall under the scope of the disclosure. Shaft 377 is arranged such that when no tube connector is connected to adapter 300, shutter 330 is closed.

Figure 4B:
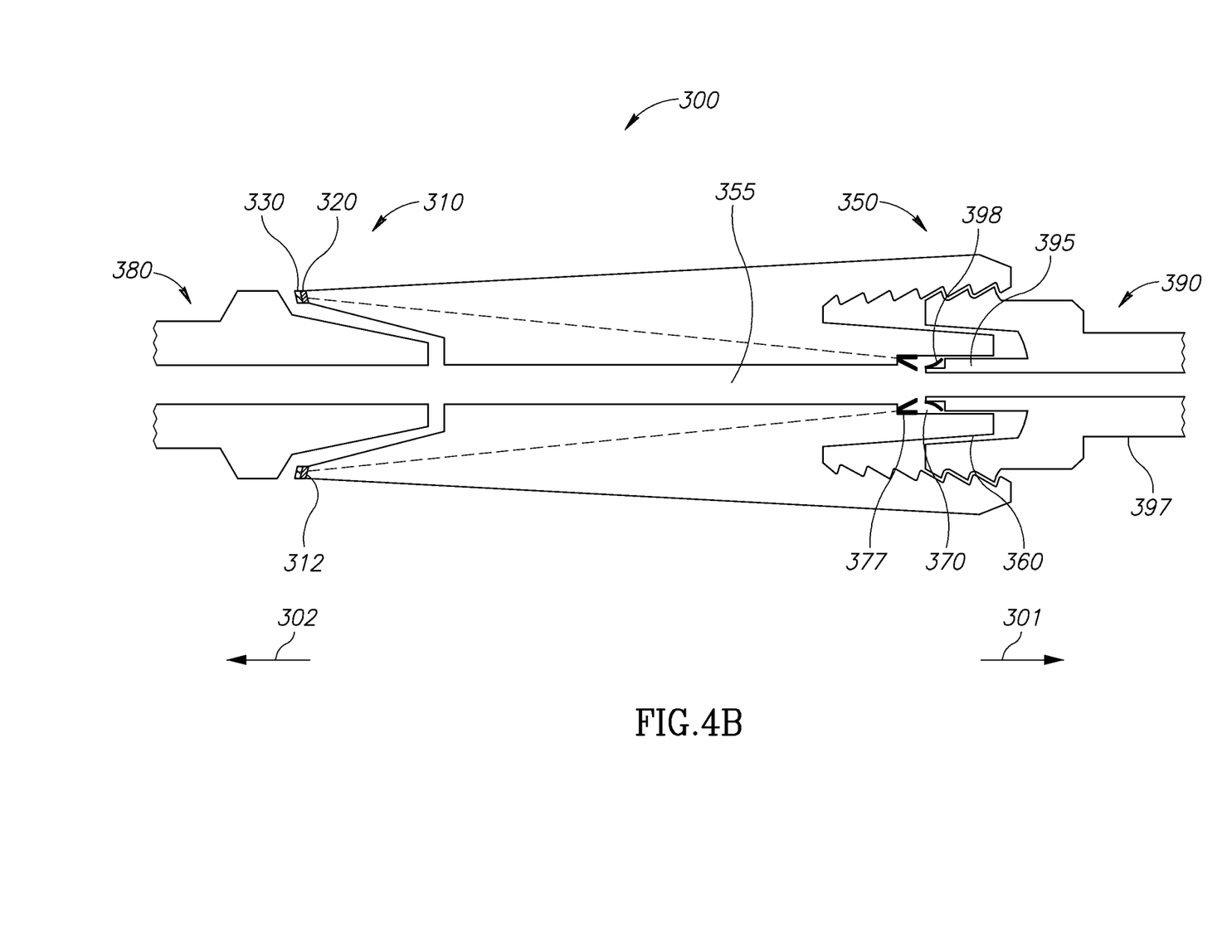
FIG. 4B schematically illustrates the adapter of FIG. 4A, interconnecting between a device connector conforming to ISO 594 and a tube connector conforming to ISO standard 80369-1 and ISO 80369-2, according to some embodiments.

Reference is now made to FIG. 4B, which schematically illustrates adapter 300, as described in FIG. 4A, interconnecting between a standard Luer device connector 380, conforming to the ISO 594 standard, and a tube connector 390 conforming to the ISO 80369-1 and ISO 80369-2 standards.

Adapter 300 includes a first end 301 (also termed the tube end), configured to be connected to tube connector 390, conforming with the new ISO 80369-1 and ISO 80369-2 standards, and a second end 302 (also termed the device end), configured to be connected to device connector 380, conforming to the ISO 594 standard. Device end 302 of adapter 300 includes a female Luer connector 310, conforming to the ISO 594 standard and tube end 301 includes a connector 350 conforming to the new ISO 80369-1 and ISO 80369-2 standards. Connector 350 includes primary Luer male connector 360, and secondary female section 370. Primary Luer male connector 360 further includes a (centralized) inner fluid flow channel 355 extending along the length of adapter 300. Thus, exhaled breath can enter first end 301 of adapter 300, through connector 350 connected to a breath sampling tube 397 via tube connector 390. In adapter 300, breath can continue its flow through inner fluid flow channel 355 to the medical device (e.g. the capnograph) through device connector 380 connected to female Luer connector 310. It is understood by one of ordinary skill in the art that only minor changes in diameter are incurred in the flow path of breath through adapter 300 and interconnected tube connector 390 and device connector 380, such that negative effects on the rise time are largely avoided.

Adapter 300 includes a reflective surface 320. Reflective surface 320 is positioned on an end face 312 (covering part or the entire of end face 312) of female Luer connector 310. However, other configurations enabling an optical path between reflective surface 320 and a connection (not shown) system including one or more light detectors configured to detect light reflected from reflective surface 320 are also applicable and as such fall under the scope of this disclosure. Adapter 300 further includes a shutter 330 positioned externally to reflective surface 320 (proximal to device end 302) on end face 312. Shutter 330 is normally closed, when no tube connector is attached to adapter 300. In effect, light impinging on end face 312 (by one or more light sources of the medical device) will be blocked by shutter 330.

Adapter 300 further includes a shaft 377 positioned on secondary female section 370 of primary Luer male connector 360. According to some embodiments, shaft 377 is positioned on the inner circumference of secondary female section 370. However, other configurations are also applicable and as such fall under the scope of the disclosure. Shaft 377 is arranged such that when tube connector 390, having a protrusion 398 on secondary male section 395 thereof, is sufficiently inserted into adapter 300, protrusion 398 pushes on shaft 377 thereby mechanically opening shutter 330. In effect, light impinging on end face 312 (by one or more light sources of the medical device) will no longer be blocked by shutter 330 and will therefore be able to reach reflective surface 320. Light reflected from reflective surface 320 can then be detected by a tube connection system of the medical device (not shown) and in effect trigger actuation of the medical device.

It is understood that shaft 377 is arranged such that if tube connector 390 is not adequately inserted into adapter 300 thus increasing the risk of disconnection and misreadings, shutter 330 is not opened. In effect no light is reflected from reflective surface 320 and the medical device is not actuated. However, according to some embodiments, complete connection may not be required.

Figure 5A:
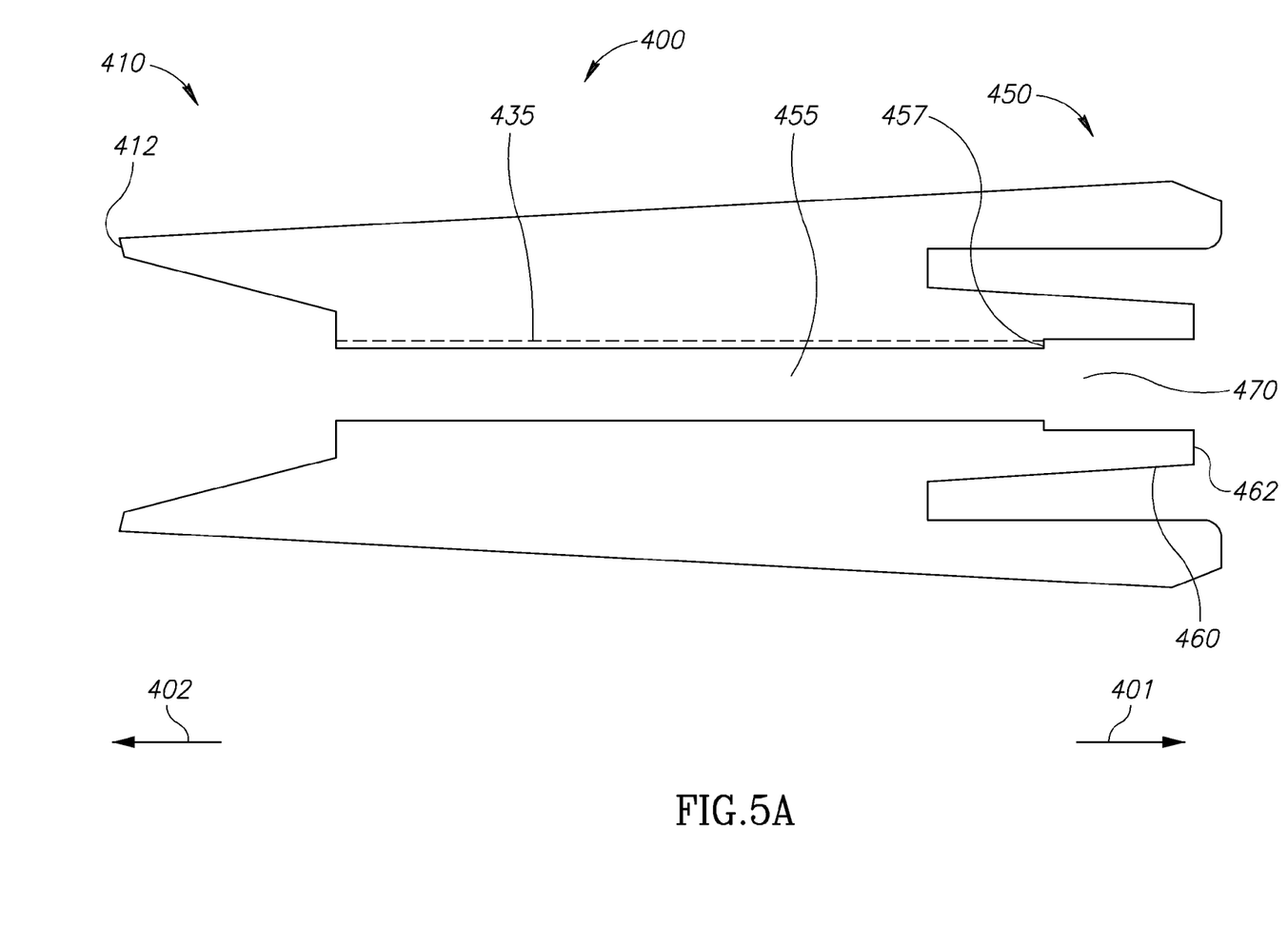
FIG. 5A schematically illustrates an adapter comprising a light transmitting media, according to some embodiments.

Reference is now made to FIG. 5A, which schematically illustrates an adapter 400, according to some embodiments. Adapter 400 includes a first end 401 (also termed the tube end), configured to be connected to a tube connector, conforming with the new ISO 80369-1 and ISO 80369-2 standards, such as but not limited to a tube connector of a breath sampling tube (not shown); and a second end 402 (also termed the device end), configured to be connected to a device connector, conforming to the ISO 594 standard, such as but not limited to a device connector of a capnograph (not shown). Device end 402 includes a female Luer connector 410, conforming to the ISO 594 standard. Tube end 401 includes a connector 450 conforming to the new ISO 80369-1 and ISO 80369-2 standards. Connector 450 includes a primary Luer male connector 460, having a form of a tapered cone. Primary Luer male connector 460 has a secondary female section 470, extending from a top distal part 462 of primary Luer male connector 460 back towards a proximal part thereof. Adapter 400 further includes a (centralized) inner fluid flow channel 455 extending along the length of adapter 400.

Inner fluid flow channel 455 has a diameter of d1. Only at a connection point between inner fluid flow channel 455 and secondary female section 470, the internal diameter is increased to form a neck 457, having an internal diameter d2, wherein d2 is larger than d1. In this manner, when gases flow from the breath sampling tube to adapter 400, through inner fluid flow channel 455 to the capnograph, only minor changes in diameter are incurred and consequently the negative effect on the rise time are largely avoided.

Adapter 400 includes a transmitting media 435. Transmitting media 435 is configured to generate an optical path between tube end 401 and device end 402 of adapter 400. When no tube connector is attached to adapter 400, light emitted on end face 412 of adapter 400 (by one or more light sources of the medical device) it will be transmitted by transmitting media 435 to tube end 401 of adapter 400 where it will disperse.

Figure 5B:
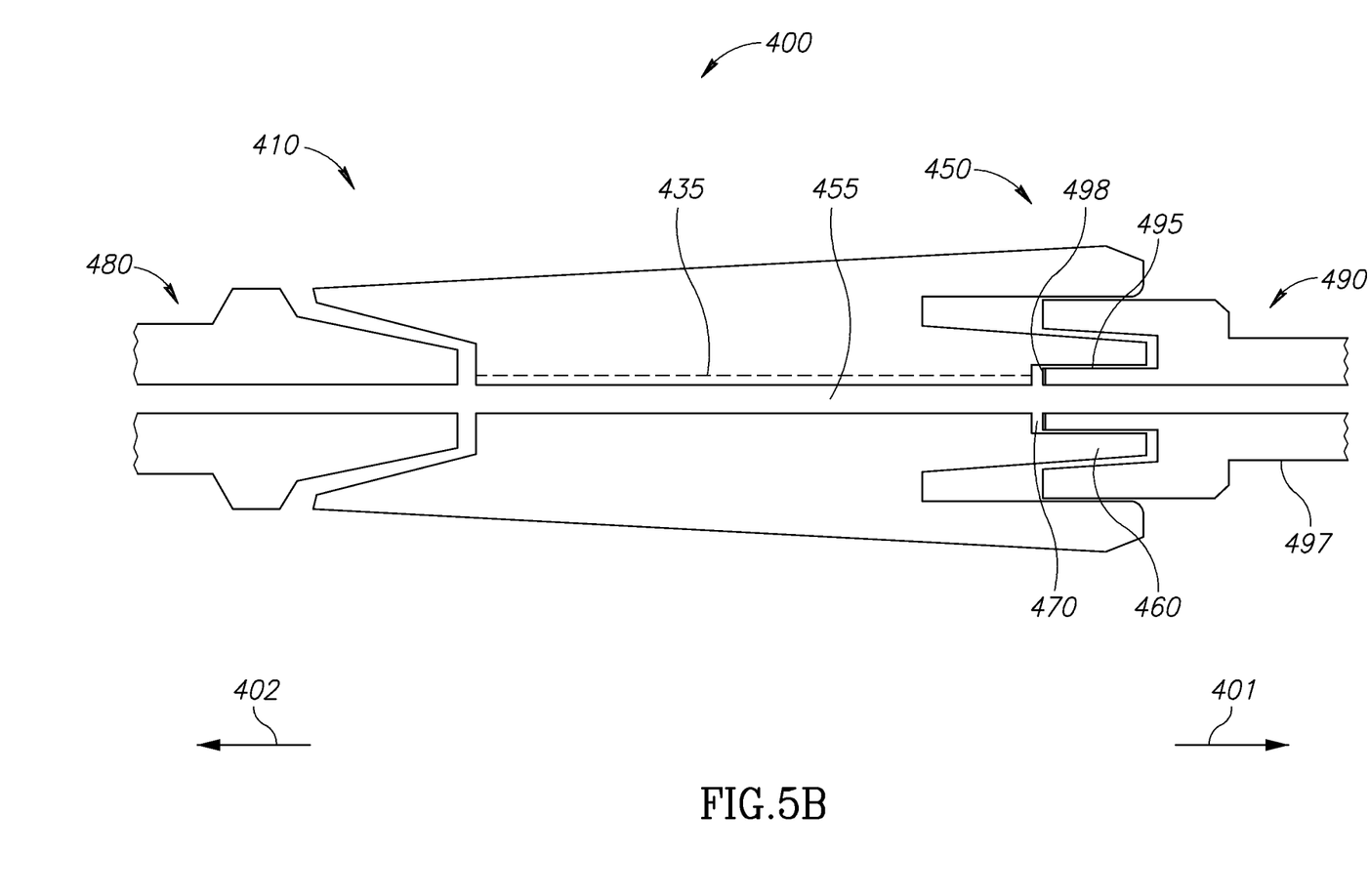
FIG. 5B schematically illustrates the adapter of FIG. 5A, interconnecting between a device connector conforming to ISO 594 and a tube connector conforming to ISO standard 80369-1 and ISO 80369-2, according to some embodiments.

Reference is now made to FIG. 5B, which schematically illustrates adapter 400, as described in FIG. 5A, interconnecting between a standard Luer device connector 480, conforming to the ISO 594 standard, and a tube connector 490 conforming to the ISO 80369-1 and ISO 80369-2 standards.

Adapter 400 includes a first end 401 (also termed the tube end), configured to be connected to tube connector 490, conforming with the new ISO 80369-1 and ISO 80369-2 standards, and a second end 402 (also termed the device end), configured to be connected to device connector 480, conforming to the ISO 594 standard. Device end 402 of adapter 400 includes a female Luer connector 410, conforming to the ISO 594 standard and tube end 401 includes a connector 450 conforming to the new ISO 80369-1 and ISO 80369-2 standards. Connector 450 includes primary Luer male connector 460, and secondary female section 470. Adapter 400 further includes a (centralized) inner fluid flow channel 455 extending along the length of adapter 400.

Thus, exhaled breath can enter first end 401 of adapter 400, through connector 450 connected to a breath sampling tube 497 via tube connector 490. In adapter 400, breath can continue its flow through inner fluid flow channel 455 to the medical device (e.g. the capnograph) through device connector 480 connected to female Luer connector 410. It is understood by one of ordinary skill in the art that only minor changes in diameter are incurred in the flow path of breath through adapter 400 and interconnected tube connector 490 and device connector 480, such that negative effects on the rise time are largely avoided.

Adapter 400 includes a transmitting media 435. Transmitting media 435 is configured to generate an optical path between tube end 401 and device end 402 of adapter 400, such that when tube connector 490 having reflective surface 498 (or any other light emitting element such as but not limited to a LED) is sufficiently inserted into adapter 400, light reflected by reflective surface 498 is transmitted by transmitting media 435 to device end 402 where it can be detected by a tube connection system of the medical device (not shown) and in effect trigger actuation of the medical device.

It is understood that transmitting media 435 is positioned such that if tube connector 490 is not adequately inserted into adapter 400, thus increasing the risk of disconnection and misreadings, light emitted from reflective surface 498 is not transmitted by transmitting media 435 to device end 402 of adapter 400. In effect no the medical device is not actuated. However, according to some embodiments, complete connection may not be required.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" or "comprising," when used in this specification, specify the presence of stated features, integers, steps, operations, elements, or components, but do not preclude or rule out the presence or addition of one or more other features, integers, steps, operations, elements, components, or groups thereof.

While a number of exemplary aspects and embodiments have been discussed above, those of skill in the art will recognize certain modifications, additions and sub-combinations thereof. It is therefore intended that the following appended claims and claims hereafter introduced be interpreted to include all such modifications, additions and sub-combinations as are within their true spirit and scope.

What is claimed is:

1. An adapter configured to interconnect a device connector of a medical device and a tube connector, said adapter comprising:
    a first end comprising a female connector;
    a second end comprising a primary male connector, having a form of a tapered cone, comprising a secondary female section extending from a top distal part of said primary male connector back towards a proximal part thereof;
    a reflective surface; and
    a shutter arranged in front of the reflective surface, such that light emitted on said shutter will be blocked from passing therethrough and from reaching said reflective surface; and
    a shaft, arranged such that when said tube connector is connected to said adapter said shaft will be pushed and said shutter be opened; wherein said adapter is configured to ensure activation of said medical device only when said tube connector is properly connected to said adapter.

2. The adapter of claim 1, wherein said shaft is positioned on said secondary female section of said primary male connector.

3. The adapter of claim 2, wherein said shaft is positioned on an inner circumference of said secondary female section.

4. The adapter of claim 1, wherein said reflective surface is positioned on an end face of said female connector.

5. The adapter of claim 4, wherein said reflective surface covers an entirety of said end face.

6. The adapter of claim 4, wherein said reflective surface covers a part of said end face.

7. The adapter of claim 4, wherein said shutter is positioned on said end face externally to said reflective surface.

* * * * *